(12) United States Patent
Chakrabortty et al.

(10) Patent No.: US 8,945,596 B2
(45) Date of Patent: Feb. 3, 2015

(54) ANTIMICROBIAL COMPOSITION

(75) Inventors: Amit Chakrabortty, Bangalore (IN); Srilaxmi Venkata Medepalli, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 177 days.

(21) Appl. No.: 13/124,715

(22) PCT Filed: Oct. 8, 2009

(86) PCT No.: PCT/EP2009/063081
§ 371 (c)(1),
(2), (4) Date: Jun. 1, 2011

(87) PCT Pub. No.: WO2010/046238
PCT Pub. Date: Apr. 29, 2010

(65) Prior Publication Data
US 2011/0223114 A1    Sep. 15, 2011

(30) Foreign Application Priority Data

Oct. 20, 2008  (IN) .................. 2254/MUM/2008

(51) Int. Cl.

| | | |
|---|---|---|
| A01N 25/00 | (2006.01) | |
| A61K 8/00 | (2006.01) | |
| A61K 8/02 | (2006.01) | |
| A61K 31/00 | (2006.01) | |
| A61K 31/05 | (2006.01) | |
| C11D 3/48 | (2006.01) | |
| A01N 31/04 | (2006.01) | |
| A01N 31/08 | (2006.01) | |
| A61K 8/34 | (2006.01) | |
| A61Q 17/00 | (2006.01) | |
| C11D 3/20 | (2006.01) | |
| A61L 2/18 | (2006.01) | |
| A61L 2/23 | (2006.01) | |
| C11D 1/04 | (2006.01) | |
| C11D 1/14 | (2006.01) | |
| C11D 1/22 | (2006.01) | |

(52) U.S. Cl.
CPC *C11D 3/48* (2013.01); *A01N 31/04* (2013.01); *A01N 31/08* (2013.01); *A61K 8/34* (2013.01); *A61K 8/347* (2013.01); *A61Q 17/005* (2013.01); *C11D 3/2037* (2013.01); *A61L 2/18* (2013.01); *A61L 2/23* (2013.01); *C11D 1/04* (2013.01); *C11D 1/146* (2013.01); *C11D 1/22* (2013.01); *Y10S 514/90* (2013.01); *Y10S 514/901* (2013.01); *Y10S 514/902* (2013.01)
USPC .............. 424/405; 424/401; 424/49; 514/729; 514/731; 514/900; 514/901; 514/902

(58) Field of Classification Search
CPC ... A01N 31/04; A01N 31/08; A01N 2300/00; A61K 8/34; A61K 8/347; A61K 2300/00

USPC ........... 424/405, 401, 49; 514/729, 731, 900, 514/901, 902
See application file for complete search history.

(56) References Cited

U.S. PATENT DOCUMENTS

| | | | |
|---|---|---|---|
| 2,196,763 A | 4/1940 | Figg, Jr. | |
| 2,359,241 A | 9/1944 | Partansky | |
| 3,256,310 A | 6/1966 | Weil | |
| 3,787,566 A * | 1/1974 | Gauvreau | ..................... 424/45 |
| 4,267,168 A | 5/1981 | Van Leuven | |
| 4,548,809 A | 10/1985 | Fung | |
| 4,966,754 A | 10/1990 | Purohit | |
| 4,992,259 A | 2/1991 | Schiraldi et al. | |
| 5,013,486 A | 5/1991 | Joshi | |
| 5,283,056 A | 2/1994 | Chung et al. | |
| 5,322,638 A | 6/1994 | Schadt et al. | |
| 5,472,684 A | 12/1995 | Nabi | |
| 5,474,712 A | 12/1995 | Dotolo | |
| 5,474,761 A | 12/1995 | Liang | |
| 5,591,708 A | 1/1997 | Richter | |
| 5,763,468 A | 6/1998 | Barranx et al. | |
| 5,817,295 A | 10/1998 | Chaudhari et al. | |

(Continued)

FOREIGN PATENT DOCUMENTS

| | | |
|---|---|---|
| CH | 692411 | 6/2002 |
| CN | 1669576 | 9/2005 |
| CN | 101036459 | 9/2007 |
| CN | 101590287 | 12/2009 |
| CN | 101601382 A | 12/2009 |
| CN | 101874531 A | 11/2010 |
| CN | 102229861 | 11/2011 |
| CN | 101601382 A | 8/2012 |
| DE | 2263126 | 7/1973 |
| DE | 3117792 | 11/1982 |

(Continued)

OTHER PUBLICATIONS

M.A. Botelho, N.A.P. Nogueira, G.M. Bastos, S.G.C. Fonseca, T.L. G. Lemos, F.J.A. Matos, D. Montenegro, J. Heukelbach, V.S. Rao and G.A.C. Brito, "Antimicrobial activity of the essential oil from Lippia sidoides, carvacrol and thymol against oral pathogens", Brazilian Journal of Medical and Biological Research (2007) 40: 349-356.*

(Continued)

*Primary Examiner* — John Pak
*Assistant Examiner* — Nathan W Schlientz
(74) *Attorney, Agent, or Firm* — Ronald A. Koatz

(57) ABSTRACT

The present invention relates to an antimicrobial composition. It particularly relates to an antimicrobial composition for cleansing or personal care. It is an object of the present invention to provide antimicrobial compositions that have relatively fast antimicrobial action. Present inventors have surprisingly found that compositions comprising selected ingredients, namely thymol and terpineol, in selective proportions provide relatively quick antimicrobial action.

5 Claims, No Drawings

(56) References Cited

U.S. PATENT DOCUMENTS

| | | |
|---|---|---|
| 5,939,050 A | 8/1999 | Iyer |
| 5,942,478 A | 8/1999 | Lopes |
| 5,965,518 A | 10/1999 | Nakatsu et al. |
| 6,048,368 A | 4/2000 | Tcheou et al. |
| 6,048,836 A | 4/2000 | Romano et al. |
| 6,066,674 A | 5/2000 | Hioki |
| 6,114,298 A | 9/2000 | Petri |
| 6,177,388 B1 | 1/2001 | Cheung et al. |
| 6,183,766 B1 | 2/2001 | Sine et al. |
| 6,190,674 B1 * | 2/2001 | Beerse et al. .................. 424/401 |
| 6,210,695 B1 | 4/2001 | Beerse et al. |
| 6,248,705 B1 | 6/2001 | Cardola et al. |
| 6,261,540 B1 | 7/2001 | Nelson |
| 6,277,805 B1 | 8/2001 | Kupneski |
| 6,323,166 B1 | 11/2001 | Kamiya |
| 6,455,086 B1 | 9/2002 | Trinh et al. |
| 6,506,707 B1 | 1/2003 | Bessette |
| 6,531,115 B1 | 3/2003 | Singh |
| 6,534,042 B2 | 3/2003 | Delli Santi et al. |
| 6,537,955 B1 * | 3/2003 | Raso et al. .................... 510/218 |
| 6,607,733 B1 | 8/2003 | Diec |
| 6,613,728 B1 | 9/2003 | Sirianni et al. |
| 6,624,126 B1 | 9/2003 | Kasuga |
| 6,645,472 B1 | 11/2003 | Anderson |
| 6,753,305 B2 | 6/2004 | Raso et al. |
| 6,841,090 B1 | 1/2005 | Serego Allighieri et al. |
| 6,861,402 B1 | 3/2005 | Miracle |
| 6,921,745 B2 | 7/2005 | Yamada et al. |
| 7,754,774 B2 | 7/2010 | Kobayashi et al. |
| 8,066,979 B1 | 11/2011 | Dickens |
| 2001/0000029 A1 | 3/2001 | Misumi |
| 2002/0002124 A1 | 1/2002 | Biedermann et al. |
| 2002/0081270 A1 | 6/2002 | Delli Santi et al. |
| 2002/0176879 A1 | 11/2002 | Dodd et al. |
| 2003/0077233 A1 | 4/2003 | Suckerman |
| 2004/0014818 A1 | 1/2004 | Boeck et al. |
| 2004/0096479 A1 | 5/2004 | Levine |
| 2004/0209795 A1 | 10/2004 | Vlad |
| 2005/0019431 A1 | 1/2005 | Modak et al. |
| 2005/0119153 A1 | 6/2005 | Burt et al. |
| 2005/0172859 A1 | 8/2005 | Nieendick et al. |
| 2005/0256021 A1 | 11/2005 | Lu |
| 2006/0045914 A1 | 3/2006 | Narayanan |
| 2006/0079414 A1 | 4/2006 | Nieendick et al. |
| 2006/0093570 A1 | 5/2006 | Duddington et al. |
| 2006/0134013 A1 | 6/2006 | Sharma |
| 2006/0141073 A1 | 6/2006 | Worrell |
| 2006/0165820 A1 | 7/2006 | Yatcilla |
| 2007/0014878 A1 | 1/2007 | Gardiner |
| 2007/0053849 A1 | 3/2007 | Doyle et al. |
| 2007/0154414 A1 | 7/2007 | Bonfiglio |
| 2007/0231295 A1 | 10/2007 | Hoppe |
| 2007/0258991 A1 | 11/2007 | Buasen et al. |
| 2007/0270321 A1 | 11/2007 | Barnhart et al. |
| 2008/0026974 A1 | 1/2008 | Barnhart et al. |
| 2008/0032908 A1 | 2/2008 | Kurtz |
| 2008/0044479 A1 | 2/2008 | Stack |
| 2008/0045491 A1 | 2/2008 | Fitchmun |
| 2008/0051312 A1 | 2/2008 | Lestage et al. |
| 2008/0064711 A1 | 3/2008 | Friedman |
| 2008/0118591 A1 | 5/2008 | Natsch |
| 2008/0194675 A1 | 8/2008 | Bettuzzi |
| 2008/0207480 A1 | 8/2008 | Pipko |
| 2008/0221003 A1 | 9/2008 | Meine et al. |
| 2008/0253976 A1 | 10/2008 | Scott |
| 2008/0274072 A1 | 11/2008 | Manolas et al. |
| 2009/0035228 A1 | 2/2009 | Modak |
| 2009/0105195 A1 | 4/2009 | O'Brien |
| 2009/0165228 A1 | 7/2009 | Kilkenny et al. |
| 2009/0317431 A1 | 12/2009 | Schaefer |
| 2010/0003198 A1 | 1/2010 | Stolmeier et al. |
| 2010/0184855 A1 | 7/2010 | Bernhardt et al. |
| 2011/0223114 A1 | 9/2011 | Chakrabortty et al. |
| 2012/0004641 A1 | 1/2012 | Bruehwiler et al. |
| 2014/0170198 A1 | 6/2014 | Franklin et al. |

FOREIGN PATENT DOCUMENTS

| | | |
|---|---|---|
| DE | 19509079 | 9/1996 |
| DE | 102004038285 | 4/2006 |
| DE | 102004038285 A1 | 4/2006 |
| EA | EP1561476 | 8/2005 |
| EP | 112141 | 12/1983 |
| EP | 0129987 B1 | 11/1986 |
| EP | 621335 | 10/1994 |
| EP | 715856 | 6/1996 |
| EP | 0916718 A1 | 10/1997 |
| EP | 0916720 | 5/1999 |
| EP | 0948892 A1 | 10/1999 |
| EP | 950399 | 10/1999 |
| EP | 0966883 A1 | 12/1999 |
| EP | 0995425 | 4/2000 |
| EP | 0995425 A2 | 4/2000 |
| EP | 1146111 | 4/2000 |
| EP | 1013261 | 6/2000 |
| EP | 1170006 | 1/2002 |
| EP | 0912098 B2 | 4/2003 |
| EP | 2018869 | 1/2009 |
| EP | 2047889 | 4/2009 |
| EP | 2348838 B1 | 5/2013 |
| ES | 2074030 A1 | 8/1995 |
| FR | 861920 | 2/1941 |
| FR | 1137 M | 5/1961 |
| FR | 1137 M | 2/1962 |
| FR | 861920 | 2/1962 |
| FR | 1356209 | 3/1964 |
| FR | 1356209 A | 3/1964 |
| FR | 2697133 | 4/1994 |
| FR | 2752730 | 3/1998 |
| GB | 366870 | 2/1932 |
| GB | 508407 | 6/1939 |
| GB | 1420946 | 1/1976 |
| GB | 2307915 | 6/1997 |
| GB | 2319181 | 5/1998 |
| GB | 2320927 | 7/1998 |
| GB | 2322552 | 9/1998 |
| GB | 2341092 | 3/2000 |
| GB | 2393911 A | 4/2004 |
| JP | 2196718 A | 8/1990 |
| JP | 2196718 A2 | 8/1990 |
| JP | 2196718 A2 | 8/1990 |
| JP | 03-011013 A2 | 1/1991 |
| JP | 9241139 A2 | 9/1997 |
| JP | 98044959 | 1/2000 |
| JP | 2000063262 A | 2/2000 |
| JP | 2003113013 | 4/2003 |
| JP | 2003113013 A2 | 4/2003 |
| JP | 2004075798 | 3/2004 |
| JP | 2005065750 | 3/2005 |
| JP | 2009196987 | 9/2009 |
| JP | 2010037272 | 2/2010 |
| JP | 2012250937 | 12/2012 |
| KR | 020030181 | 4/2002 |
| KR | 20020030181 A | 4/2002 |
| KR | 20020032949 A | 5/2002 |
| KR | 100885511 | 2/2009 |
| KR | 20100123424 | 11/2010 |
| KR | 20120093607 | 8/2012 |
| RU | 2277923 | 6/2006 |
| RU | 2277923 C2 | 6/2006 |
| SE | CH692411 | 6/2002 |
| SU | 1644963 A1 | 4/1991 |
| WO | WO9218091 | 10/1992 |
| WO | WO9512379 | 5/1995 |
| WO | WO9611694 | 4/1996 |
| WO | WO9715277 | 5/1997 |
| WO | WO9725106 | 7/1997 |
| WO | WO9730586 A1 | 8/1997 |
| WO | WO9731092 A1 | 8/1997 |
| WO | WO9731093 A1 | 8/1997 |
| WO | WO9801524 | 1/1998 |
| WO | WO9802044 A1 | 1/1998 |
| WO | WO9802139 | 1/1998 |
| WO | WO9811867 | 3/1998 |
| WO | WO9824314 | 6/1998 |

(56) References Cited

FOREIGN PATENT DOCUMENTS

| | | |
|---|---|---|
| WO | WO9844959 A1 | 10/1998 |
| WO | 9855093 | 12/1998 |
| WO | WO9854279 | 12/1998 |
| WO | WO9855080 A2 | 12/1998 |
| WO | WO9855092 A1 | 12/1998 |
| WO | WO9855094 | 12/1998 |
| WO | WO9855095 A1 | 12/1998 |
| WO | 9936033 | 7/1999 |
| WO | WO9952360 | 10/1999 |
| WO | WO9958631 | 11/1999 |
| WO | WO0000166 | 1/2000 |
| WO | WO0051436 | 9/2000 |
| WO | WO0061106 | 10/2000 |
| WO | 0170215 | 9/2001 |
| WO | WO0167868 | 9/2001 |
| WO | WO0179409 | 10/2001 |
| WO | WO02065859 A1 | 8/2002 |
| WO | WO02096435 | 12/2002 |
| WO | WO03010273 | 2/2003 |
| WO | WO03034994 | 5/2003 |
| WO | WO03037270 A2 | 5/2003 |
| WO | WO03050224 | 6/2003 |
| WO | WO03091375 | 11/2003 |
| WO | WO03095600 | 11/2003 |
| WO | WO2004006679 | 1/2004 |
| WO | WO2004032886 | 4/2004 |
| WO | WO2004035723 A1 | 4/2004 |
| WO | WO2005094385 | 10/2005 |
| WO | WO2006012715 | 2/2006 |
| WO | WO2006053458 A1 | 5/2006 |
| WO | WO2006109898 | 10/2006 |
| WO | WO2007065538 | 6/2007 |
| WO | WO2007110790 A1 | 10/2007 |
| WO | WO 2007/125216 A1 * | 11/2007 |
| WO | WO2007125216 A1 | 11/2007 |
| WO | WO2008017484 A1 | 2/2008 |
| WO | 2008/028278 | 3/2008 |
| WO | WO2008034549 | 3/2008 |
| WO | WO2008035101 A2 | 3/2008 |
| WO | WO2008035101 A3 | 3/2008 |
| WO | WO2008060130 | 5/2008 |
| WO | 2008/088827 | 7/2008 |
| WO | WO2008085446 A2 | 7/2008 |
| WO | WO2008125884 | 10/2008 |
| WO | WO2008157847 | 12/2008 |
| WO | WO2009000097 | 12/2008 |
| WO | WO2009083521 A2 | 7/2009 |
| WO | WO2009083521 A3 | 7/2009 |
| WO | WO2009085058 | 7/2009 |
| WO | WO2009113910 | 9/2009 |
| WO | WO2010046238 | 4/2010 |
| WO | WO2011023582 | 3/2011 |
| WO | WO2011036048 | 3/2011 |
| WO | WO2011039630 | 4/2011 |
| WO | WO2011151169 | 12/2011 |
| WO | WO2011151171 | 12/2011 |

OTHER PUBLICATIONS

A. Jose, B. Coco, S. Milligan, J. Cross, J. Bagg and G. Ramage, "Candida biofilms in denture stomatitis: novel detection and treatment methods", The Pan European Federation of the International Association for Dental Research (Sep. 11, 2008).*
Dimitrijevic, et al., A study of the synergistic antilisterial effects of a sub-lethal dose of lactic acid and essential oils from *Thymus vulgaris* L., *Rosmarinus officinalis* L. and *Origanum vulgare* L., Food Chemistry 104 (2007), pp. 774-782, Elsevier.
Achi, "Composition and Antibacterial Activities of *Tetrapleura tetraptera* Taub Pod Extracts", Research Journal of Microbiology, 2006, vol. 1 No. 5, pp. 416-422.
Friedman et al., "Antibacterial Activities of Naturally Occurring Compounds Against Antibiotic-Resistant *Bacilllus cereus* Vegetative Cells and Spores, *Escherichia coli*, and *Staphylococcus aureus*", Journal of Food Protection, 2004, vol. 67, No. 8, pp. 1774-1778.
Van der Wolf, "Disinfection of vegetable seed by treatment with essential oils, organic acids and plant extracts" Seed Science and Technology, 2008, voumne 36, pp. 76-88.
PCT International Search Report in PCT application PCT/EP2009/063081 dated Jan. 1, 2010 with Written Opinion.
European Search Report in EP application EP 09 15 3930 dated Jul. 27, 2009.
Henkel Opposition against EP Patent No. 2 348 838 B1 dated Feb. 7, 2014.
Biersdorf Opposition against EP Patent No. 2 348 838 B1 dated Feb. 6, 2014.
IPRP in PCTEP2012074399, Jul. 10, 2014, pp. 1-20, WO.
IPRP2 in PCTEP2012074409, Jul. 10, 2014.
IPRP2 in PCTEP2012074416, Jul. 10, 2014.
Biologically Active Substances of Plant Origin, Russian Academy of Sciences, 2001.
Banayeva et al., "A Study of the Chemical Composition of the Essential Oil of Representatives of the Genus Thymus L. Growing in the Altai", Vegetable feed chemistry, 1999, vol. 3, pp. 41-48 with Translation.
Gablin, Balsamic fragrances Lemon thyme, Handmade Soaps, 2007, p. 84 with Translation.
Zhigzhitzhapova et al., "The Chemical Composition of the Essential Oil of Baikal Thyme, Thymus Baicalensis Serg., Growing in the Zabaikal Territory", Vegetable fee chemistry, 2008, vol. 1, pp. 73-76 with Translation.
Yu et al., "The study of the chemical composition of an essential oil of the genus Thymus L. representaives grown in Altai", Vegetable feed chemistry, 1999, No. 3, pp. 41-48.
Zhigzhitzhanova et al., "Chemical composition of an essential oil of Baikal thyme Thymus Baikalensis Serg. grown in Transbaikar", Vegetable feed chemistry, 2008, No. 1, pp. 73-76.
Translation of Eurasian Written Opinion for Application No. 201100656 (PCT/EP2009/063081) dated Dec. 11, 2012.
A. Perez-Vasquez et al., Antimicrobial activity and chemical composition of the essential oil of *Hofmeisteria Schaffneri*, Journal of Pharmacy and Pharmacology, Aug. 5, 2010, 579-586, vol. 63.
Abdeslam Jaafari, Hassan Ait Mouse, El Mostapha Rakib et al, Chemical composition and antitumor activity of different wild varieties of Moroccan thyme, Brazilian Journal of Pharmacognosy, Aug. 27, 2007, 477-491, 17 (4).
Burt et al, Essential oils: their antibacterial properties and potential application in foods—a review, Int J of Food Microbiology, 2004, 223-253, 94.
Cen Members, Chemical disinfectants and antiseptics—Quantitative suspension test for the evaluation of bactericidal activity of chemical . . . , European Standard, Jan. 1, 1997, 1-18, EN 1276.
Davies A., Action of Biguanides, Phenols and detergents on *Escherichia coli* and its spheroplasts, Action of Biguanides, 1969, 233-243, 32.
Evandro Leite De Souza, Interference of heating on the antimicrobial activity and chemical composition of Origanum vulgare L. (Lamiaceae) essential oil, Interference of heating on the antimicrobial activity and chemical composition of Origanum vulgare L. (Lamiaceae) essential oil, Apr. 1, 2008, 1-7, vol. 28, No. 2.
Figueredo et al, Studies of mediterranean oregano populations. VIII-Chemical composition of essential oils of oreganos of various origins, Flavour and Fragrance Journal, May 9, 2005, 134-139, 21.
Hong S, Antimicrobial Activity of Tyramine Derivatives, Antimicrobial Activity of Tyramine Derivatives, Oct. 29, 2000, NA, NA.
Jalali-Heravi et al, Analysis of Iranian rosemary essential oil: application of gas chromatography-mass spectrometry combined with chemometrics, Journal of Chromatography A, Mar. 21, 2011, 2569-2576, 1218.
Karabit et al, Studies on the evaluation of preservative efficacy III. The determination of antimicrobial characteristics of benzalkonium chloride, Int J of Pharmaceutics, 1988, 141-147, 46.
Kirchner et al, Chemical composition and antimicrobial activity of *Hedyosmum brasiliense*Miq., Chloranthaceae, essential oil, Brazilian Journal of Pharmacognosy, Jan. 11, 2010, 692-699, 20(5).
Kisgyorgy et al, Essential oil of the more important indigenous *Thymus*species occurring in the composition of Serpylli herba, Farmakognoziai Tansz., Jan. 1, 1983, 124-130, 29.

(56) References Cited

OTHER PUBLICATIONS

Kubo et al, Antimicrobial activity of anethole and related compounds from aniseed, Journal of the Science of Food and Agriculture, 2008, 242-247, 88.

Leung A Y; Foster, Encyclopedia of common and natural ingredients used in food, drugs and cosmetics, Cinnamon (and Cassia), Jan. 1, 1996, pp. 167-170,260-264,393-397,405-408,492-494,510-511, ISBN: 978-0-471-50826-7.

M. 5EBESAN, Analysis of the I,II Essential Oils from Thyme (*Thymus vulgaris L*) and from Peppermint (*Mentha piperita L*), Analysis of the I,II Essential Oils from Thyme and from Peppermint, Dec. 31, 2008, 212-214, Retrieved from the Internet.

Mah J H, *Paenibacillus*tyraminigenes sp. nov. isolated from Myeolchi-jeotgal. a traditional Korean salted and fermented anchovy, *Paenibacillus*tyraminigenes sp. nov. isolated from Myeolchi-jeotgal., Oct. 31, 2008, pp. 209-214, vol. 127. No. 3.

Majnooni et al, Chemical composition, cytotoxicity and antioxidant activities of the essential oil from the leaves of *citrus aurantium L.*, African Journal of Biotechnology, May 1, 2012, 498-503, 11(2).

Miladinovie et al, Investigation of the chemical composition—antibacterial activity relationship of essential oils by chemometric methods, Anal Bioanal Chem, Mar. 3, 2012, 1007-1018, 403.

Mintel, Antibacterial Fluride Toothpaste, Antibacterial Fluride Toothpaste, Nov. 2007, NA, NA, NZ.

Mintel, Mouth Rinse, Mouth Rinse, Oct. 2007, NA, NA, GB.

Naigre Ruth, Comparison of antimicrobial properties of monoterpenes and their carbonylated products, Comparison of antimicrobial properties of monoterpenes and their carbonylated products, 1996, 275-277, vol. 62, No. 3.

Oyedemi et al., The proposed mechanism of bactericidal action of eugenol, a-terpineol and y-terpinene against *listeria monocytogened, streptococcus pyogenes, proteurs vulgaris and escherichia coli*, African Journal of Biotechnology, Apr. 6, 2009, 1280-1286, 8(7).

Rossi et al, Chemical fingerprinting and bioactivity of Amazonian Ecuador *croton lechleri*Mull. Arg. (Euphorbiaceae) stem bark essential oil: A new functional food ingredient?, Food Chemistry, Jun. 1, 2011, 837-848, 126.

Sagoo Sk, Chitosan potentiates thE antimicrobial action of sodium benzoate on spoilage yeasts, Chitosan and Benzoate, Jan. 3, 2008, 168-172, 34—No. 3.

Sato et al, Antimicrobial effect of trans-cinnamaldehyde, (-)-perillaldehyde, (-)-citronellal, citral, eugenol and carvacrol on airborne microbes using an airwasher, Biol Pharm bull, 2006, 2292-2294, 29(11).

Sawamura et al, Characteristic odor components of *citrus reticulata*blance (Ponkan) cold-pressed oil, Biosci. Biotechnol. Biochem., Apr. 16, 2004, 1690-1697, 68(8).

Shixiang, Anticorrosive functions of convention flavors and fragrances, Toothpaste Industry, 2000, 23-27, 2, CN.

Singh et al., Antioxidant and antimicrobial activities of essential oil and various oleoresins of *Elettaria cardamomum*(seeds and pods), Journal of the Science of Food and Agriculture, Mar. 6, 2007, 280-289, 88.

Tian et al, Chemical composition and antifungal activity of essential oil from *cicuta virosa L.*var. latisecta celak, International Journal of Food Microbiology, Jan. 1, 2011, 464-470, 145.

Tippayatum et al, Antibacterial activities of thymol, eugenol and nisin against some food spoilage bacteria, Nat Science, 2007, 319-323, 41.

Wang, Synergistric Antimicrobial Activities of Natural Oils with Chitosan Films, Journal of Agricultural and Food Chemistry, Oct. 29, 2011, 12411-12419, vol. 59 No. 23, ACS Publications, US.

Younhee Byun et al., Analysis of Composition and Activity of Essential Oil from *Chrysanthemum zawadskii*var. latilobum and *C. indicum*against Antibiotic-Resistant Pathobenic Bacteria, Natural Product Sciences, Jun. 16, 2008, 138-142, vol. 14-No. 2.

Yu et al., Chemical composition and antimicrobial activity of the essential oil of *Scutellaria barbata*, Phytochemistry 65 (2004), Sep. 5, 2003, 881-884, 65.

Zrira et al, Chemical composition of the essential oil of nine eucalyptus species growing in Morocco, Flavour and fragrance journal, Apr. 2, 2004, 172-175, 19.

Castor Oil, Wikipedia (website), pp. 1-4 May 2, 2014.

Budavari (Editor), An Encyclopedia of Chemicals, Drugs, and Biologicals. The Merck Index, 1996, 1568, 12th Edition, Merck Research Laboratories, Whitehouse Station, US.

Gablin, Balsamic fragrances Lemon thyme, Handmade Soaps, Jul. 18, 2007. 84, RU.

Umback et al., Georg Thieme Verlag, Kosmetik, 1995, 360-369; DE.

\* cited by examiner

ANTIMICROBIAL COMPOSITION

The present invention relates to an antimicrobial composition. It particularly relates to an antimicrobial composition for personal cleaning, oral care or hard surface cleaning applications.

Sanitizing and disinfecting soap compositions comprising chlorine-based antimicrobial agent such as triclosan are known. Such compositions require rather long contact time to provide efficacious antimicrobial action. In practice, users, in particular children, do not spend long time in cleaning and as a result, cleaning with such compositions does not provide adequate prevention from surface or topical infection or adequate protection against diseases. The user, in spite of cleaning hands, is likely to have skin with relatively inadequate bacterial removal and may cause contamination of further animate and/or inanimate surfaces and lead to spreading of pathogens and consequent diseases. Users in general and children in particular who wash contaminated hands before meals with slow-acting antimicrobial compositions for relatively short time are at risk of contacting diseases. Further, many antimicrobial actives in addition to abrasives are included in oral care compositions like dentifrices but these actives generally require several minutes if not hours before effective antimicrobial action is effected. People often brush their teeth or rinse their mouth for very short periods of time e.g. of the order of 1 minute or less, thus making such compositions quite ineffective in providing the desired benefit.

Similarly in the area of hard surface cleaning, e.g. cleaning of floors, table tops or utensils, the antimicrobial in the compositions are in contact with the substrate for less than a few minutes after which the surface is either wiped off or rinsed with water. These short time scales of cleaning action are ineffective in providing the desired benefit since most known antimicrobials commonly used in such products take several hours to provide the desired kill of microbes.

Therefore, there is a need of providing a composition that gives relatively more efficacious antimicrobial action when cleaning period is relatively small, typically about 5 minutes or less, preferably lesser than 2 minutes and in many cases less than one minute or sometimes as low as 15 seconds or lesser.

Present inventors have surprisingly found that compositions comprising selected ingredients, namely thymol and terpineol, in selective proportions provide relatively quick antimicrobial action.

GB366870 (Namlooz Vennootschap, 1931) describes a process of perfuming toilet soaps. Two different examples of soap perfumes, one comprising thymol and the other comprising terpineol are described. There is no disclosure of a specific soap composition comprising mixture of thymol and terpineol.

U.S. Pat. No. 6,534,042 (Pfizer, 2003) describes an oral care composition comprising from 0.01 to 5% by weight of citrus flavour or citrus flavour ingredient and from 0.01 to 5% by weight a phenolic selected from the group consisting of menthol eucalyptol, methyl salicylate, thymol, triclosan and mixtures thereof, and an orally acceptable carrier. The citrus flavour ingredient is selected from group consisting of limonene, citral, cadiene, decylaldehyde, linalool, terpineol, linalyl esters, terpinyl acetate, citronellol, alpha-terpinene, 2-dodecanal, alpha-pinene, beta-pinene, 3-penternal, decanal, and C8 to C10 and C12 aldehydes, acids, and esters found in citrus flavours and mixtures thereof. The oral care composition is said to be useful in retarding development of plaque, treating gingivitis and reducing viable population of microorganisms in oral cavity. There is no disclosure of a specific composition comprising thymol and terpineol.

GB508407 (Shepherd, 1938) describes an antiseptic product and method of preparation thereof comprising the steps of mixing salol and thymol in weight ratio of 1:3, melting the mixture and cooling to form crystals. An example of composition comprising 59 parts of the crystals, 41 parts of terpineol, 200 parts of red turkey oil and 200 parts of water is described. The composition described in this document comprises about 8% by weight thymol and about 8% by weight terpineol and is said to be particularly useful for disinfection of air. Similarly WO2008/088827 discloses several hundred embodiments of compositions for controlling insects and pests, one of which has thymol and terpineol at similar high concentrations.

US 2004/0014818 (Boeck) discloses a bactericidal preparation in the form of a solution, cream or ointment compounded from photosynthesized hydrocarbons, isolates from hydrocarbons, 2-hydroxy-1-isopropyl-4-methyl benzene (thymol) and butylated hydroxytoluene and exemplifies many compositions, each having from 10 to 20 compounds having anti-bacterial efficacy. This patent publication does not teach that a specific combination of terpineol and thymol in specific amounts provides fast acting anti-microbial efficacy.

None of the patents cited above address the problem of slow-acting antimicrobial compositions.

U.S. Pat. No. 5,965,518 (Nakatsu et al, 1999) describes a fragrance composition having antimicrobial activity comprising between 3 to 20% by weight of a phenolic compound and between 20 and 80% by weight of a non-aromatic terpenoid. Examples of phenolic compounds include amyl salicylate, cavacrol, dihydroeugenol, eugenol, hexyl eugenol, hexyl salicylate, isoeugenol, methyl eugenol, methyl isoeugenol, methyl salicylate, tert butyl cresol, thymol, and vanillin. Examples of non-aromatic terpenoid compounds include cedrene, cineole, citral, citronellal, citronellol, cymene, paradihydrolinalool, dihydromyrcenol, farnesol, geraniol, hexyl cinnamaldehyde, hydroxycitronallol, hydroxycitronellal, isocitral, limonene, linalool, longifolene, menthol, nerol, nerolidiol, phellendrene, terpinene, terpinenol, and tetrahydromyrcenol. There is no disclosure of a specific composition comprising thymol and terpineol. The compositions reduce microbial number by at least 1.5 log cfu/mL within 5 minutes when used at about 0.25% concentration. Although there is some improvement in speed of antimicrobial action, there is still an on-going need for developing compositions with relatively fast antimicrobial action.

It is an object of the present invention to overcome or ameliorate at least one of the disadvantages of the prior art, or to provide a useful alternative.

Another object of the present invention is to provide antimicrobial compositions that have relatively fast antimicrobial action.

According to the first aspect of the present invention, there is provided an antimicrobial composition comprising:
(a) 0.01 to 5% by weight thymol,
(b) 0.01 to 5% by weight terpineol, and
(c) a carrier.

According to another aspect of the invention there is provided a method of disinfecting a surface comprising the steps of:
(a) applying a composition of the first aspect of the invention to the surface; and
(b) rinsing the surface with a suitable solvent.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated.

Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

The antimicrobial composition comprises thymol, terpineol and a carrier. Various components of the antimicrobial composition are described below. The compositions of the present invention are preferred for non-therapeutic use, and more particularly preferred for use in cleaning surfaces of human body including skin, hair or oral cavity or for hard surface cleaning applications.

The antimicrobial composition comprises preferably 0.05 to 5%, more preferably 0.1 to 1%, and most preferably 0.1 to 0.4% by weight thymol. Most of the useful antimicrobial compositions of the present invention have thymol higher than 0.05 and lesser than 0.3% by weight thymol. These preferred concentration ranges of thymol are important since below the preferred lower concentration of thymol, the desired fast acting antimicrobial kinetics in combination with terpineol would not be met. At concentrations higher than the higher preferred concentrations of thymol, when in combination with terpineol, while the kinetics of action would not be compromised, the present inventors have found that unlike in therapeutic/pesticidal/herbicidal applications where sensorial aspects are not critical, in the present application, which is preferably a personal cleaning, oral care or hard surface cleaning applications, the product is in contact with hands, mouth or other body parts, the sensorial aspects like smell and skin feel would be compromised. Thymol may be added to the antimicrobial composition in purified form.

Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*.

The structures of thymol and its isomer carvacrol are given below:

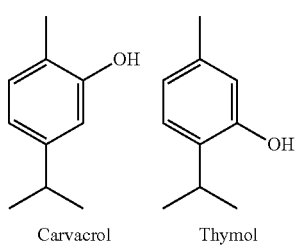

Carvacrol    Thymol

The antimicrobial composition comprises preferably 0.05 to 5%, more preferably 0.1 to 1%, and most preferably 0.4 to 0.6% by weight terpineol. Most of the useful fast acting antimicrobial compositions of the present invention have terpineol higher than 0.05 and lesser than 1% by weight terpineol. These preferred concentrations ranges of terpineol are important for the same reasons as the preferred concentration ranges of thymol in meeting the desired fast acting antimicrobial kinetics while not being sensorially unpleasant when used in products for personal cleaning, oral care or hard surface cleaning applications. The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form.

Alternatively pine oil comprising terpineol may be added to the antimicrobial composition.

The structure of a terpineol compound is given below:

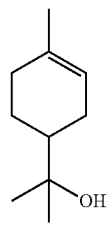

The antimicrobial composition comprises a carrier. The carrier is selected from the group consisting of water, oil, solvent, inorganic particulate material, starch and mixtures thereof. The carrier is preferably from 0.1 to 99% by weight of the composition. The antimicrobial composition may be in form of a solid, liquid, gel, paste or soft solid and the carrier may be selected by a person skilled in the art depending on the format of the antimicrobial composition.

The examples of inorganic particulate materials include clay, talc, calcite, dolomite, silica, and aluminosilicate. The examples of oils include mineral oils, vegetable oils, and petroleum-derived oils and waxes. The examples of solvents include alcohols, ethers and acetone.

The starch may be natural starch obtained from food grains or may be a modified starch.

Particularly preferred carriers are water or oil/solvent, more preferred a carrier being a mixture of water and oil. In most of the envisaged applications like personal care/washing, oral care and hard surface cleaning, the antimicrobial composition may be formulated in an aqueous base (water being carrier) e.g. products in gel format or in purely oil/solvent base e.g. products in anhydrous stick form or propellant containing products. However, most preferred product format has an emulsion base (water and oil being the carrier) e.g. soap products in liquid, solid, lotion or semisolid form for hand wash, face wash, body wash, or shaving applications; toothpaste/dentifrices for oral care applications or products for hard surface cleaning in bars or liquids form. Thus a particularly preferred antimicrobial composition comprises
a. higher than 0.05 and lesser than 0.3% by weight thymol;
b. higher than 0.05 and lesser than 1% by weight terpineol; and
c. a carrier.

The antimicrobial composition preferably comprises 1 to 80% surfactant. In general, the surfactants may be chosen from the surfactants described in well known textbooks like "Surface Active Agents" Vol. 1, by Schwartz & Perry, Interscience 1949, Vol. 2 by Schwartz, Perry & Berch, Interscience 1958, and/or the current edition of "McCutcheon's Emulsifiers and Detergents" published by Manufacturing Confectioners Company or in "Tenside-Taschenbuch", H. Stache, 2nd Edn., Carl Hauser Verlag, 1981. Any type of surfactant, i.e. anionic, cationic, nonionic, zwitterionic or amphoteric can be used.

A particularly preferred surfactant is soap. Soap is a suitable surfactant for personal washing applications of the antimicrobial composition of the invention. The soap is preferably C8-C24 soap, more preferably C10-C20 soap and most preferably C12-C16 soap. The soap may or may not have one or more carbon-carbon double bond or triple bond. The cation of the soap can be alkali metal, alkaline earth metal or ammonium. Preferably, the cation of the soap is selected from sodium, potassium or ammonium. More preferably the cation of the soap is sodium or potassium.

The soap may be obtained by saponifying a fat and/or a fatty acid. The fats or oils generally used in soap manufacture may be such as tallow, tallow stearines, palm oil, palm stearines, soya bean oil, fish oil, castor oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soybean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources and generally comprise about 1-8% myristic acid, about 21-32% palmitic acid, about 14-31% stearic acid, about 0-4% palmitoleic acid, about 36-50% oleic acid and about 0-5% linoleic acid. A typical distribution is 2.5% myristic acid, 29% palmitic acid, 23% stearic acid, 2% palmitoleic acid, 41.5% oleic acid, and 3% linoleic acid. Other similar mixtures, such as those from palm oil and those derived from various animal tallow and lard are also included.

Coconut oil refers to fatty acid mixtures having an approximate carbon chain length distribution of 8% $C_8$, 7% $C_{10}$, 48% $C_{12}$, 17% $C_{14}$, 8% $C_{16}$, 2% $C_{18}$ 7% oleic and 2% linoleic acids (the first six fatty acids listed being saturated). Other sources having similar carbon chain length distributions, such as palm kernel oil and babassu kernel oil, are included within the term coconut oil.

A typical fatty acid blend consisted of 5 to 30% coconut fatty acids and 70 to 95% fatty acids ex hardened rice bran oil. Fatty acids derived from other suitable oils/fats such as groundnut, soybean, tallow, palm, palm kernel, etc. may also be used in other desired proportions. The soap, when present in solid forms of the present invention, is present in an amount of 30 to 90%, preferably from 50 to 85%, more preferably 55 to 75% by weight of the composition. The soap, when present in liquid forms of the composition is present in 0.5 to 20%, preferably from 1 to 10% by weight of the composition.

The antimicrobial composition of the invention is useful in hard surface cleaning applications. In such applications preferred surfactants are nonionic surfactants, such as C8-C22, preferably C8-C16 fatty alcohol ethoxylates, comprising between 1 and 8 ethylene oxide groups when the product is in the liquid form. When the product is in the solid form for hard surface cleaning applications surfactants are preferably selected from primary alkyl sulphate, secondary alkyl sulphonates, alkyl benzene sulphonates, or ethoxylated alkyl sulphates. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16. Suitable surfactant concentrations in liquid forms of hard surface cleaning application are generally from about from 0.5 to 10%, preferably from 1 to 5% by weight of the composition. In solid compositions, surfactant is preferably present in 5 to 40%, preferably from 10 to 30% by weight of the composition.

The antimicrobial composition of the invention is useful in oral care compositions e.g. in a dentifrice/toothpaste or oral rinse product. In such applications, preferred surfactants are anionic, nonionic or amphoteric in nature, preferably anionic or amphoteric. Anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear C10~018 chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Thus, in a highly preferred aspect, the antimicrobial compositions include soap, alkyl sulphate or linear alkyl benzene sulphonate as the surfactants.

The inventors have determined to their utter surprise that while thymol alone and terpineol alone do not individually provide the fast antimicrobial kinetic action, a combination of thymol and terpineol at the selective concentrations provides a synergistic antimicrobial action which is especially important in a wash off processes where the contact time of the antimicrobial actives with the surface is low, i.e. of the order of less than 5 minutes, preferably less than 2 minutes, further more preferably less than a minute and in many cases less than 15 seconds. Fortuitously such wash off processes include a surfactant for the cleaning action. To the further surprise of the inventors, while the surfactant alone does not provide the fast antimicrobial kill at the concentration present in wash off processes, it provides for further improvement in extent of reduction in microbial counts on the surface in short period of time when surfaces are washed with a composition comprising terpineol, thymol and additionally surfactant. Thus, while on the one hand surfactant is generally known to be responsible for washing off dirt and also antimicrobial actives used in the composition, in the present invention, it provides a highly useful additional benefit in that it enhances the reduction of microbial count in a composition comprising a combination of thymol and terpineol alone.

A further additional advantage of the present invention is that it is observed that surfaces treated with a composition comprising terpineol and thymol, surprisingly enable continued protection of the surface against growth of microbes for a substantial period of time thereafter.

The composition may further comprise various additional ingredients known to a person skilled in the art. Such additional ingredients include but are not limited to: perfumes, pigments, preservative, emollients, sunscreens, emulsifiers, gelling agents, or thickening agents.

The antimicrobial composition may be in form of a solid, a liquid, a gel or a paste. A person skilled in the art can prepare compositions in various formats by choosing one or more carrier materials and/or surfactant. The antimicrobial compositions of the present invention are useful for cleansing and care, in particular for skin cleansing and skin care. It is envisaged that the antimicrobial composition can be used as a leave-on product or a wash-off product, preferably a wash-off product. The antimicrobial composition of the present invention can also be used for cleansing and care of hard surfaces such as glass, metal, plastic and the like.

According to one aspect water is a preferred carrier. When water is present, it is preferably present in at least 1%, more preferably at least 2%, further more preferably at least 5% by weight of the composition. When water is the carrier, a preferred liquid composition comprises:

a. 0.05 to 5% by weight thymol,
b. 0.05 to 5% by weight terpineol
c. 10 to 99.9% by weight water, and;
d. 1 to 30% by weight surfactant.

The liquid antimicrobial composition is useful for skin cleansing, in particular for hand wash or a face wash.

When water is the carrier, a preferred solid composition comprises:

a. 0.05 to 5% by weight thymol,
b. 0.05 to 5% by weight terpineol,
c. 5 to 30% by weight water, and;
d. 30 to 90% by weight surfactant.

The solid antimicrobial composition is preferably in form of a shaped solid, more preferably a bar. The solid antimicrobial composition is particularly useful for skin cleansing in particular for hand wash or a face wash.

According to another aspect, inorganic particulate material is also a suitable carrier. When inorganic particulate material is the carrier, the antimicrobial composition is in a solid form. Preferably the inorganic particulate material is talc. When the inorganic particulate material is talc, the solid antimicrobial composition is particularly useful as a talcum powder for application on face or body.

According to a further aspect, solvent is a preferred carrier. Although any solvent can be used, alcohol is a preferred solvent. Short chain alcohols, in particular ethanol and propanol, are particularly preferred as carrier for an antimicrobial wipe or an antimicrobial hand sanitizer composition.

According to another aspect of the present invention there is provided a method of disinfecting a surface comprising the steps of:

(a) applying a composition of the first aspect of the invention on to the surface; and
(b) rinsing the surface with a suitable solvent.

The solvent for rinsing the surface is preferably water but could also be a mixture of water and alcohol. The word rinsing herein includes the act of wiping the surface with a suitable wipe. Thus the surface e.g hand, face, body, oral cavity or any hard surface e.g. a utensil is first contacted with the composition of the invention. It is then rinsed preferably with sufficient amounts of water after a pre-determined period of time to remove any visible or sensory reside of the composition. Alternately an alcohol wipe or a water/alcohol impregnated wipe may be used to wipe the surface to be visibly free of the anti-microbial composition. The step of rinsing the substrate is preferably carried out less than 5 minutes, preferably less than 2 minutes, further more preferably less than a minute and in many cases less than 15 seconds after the step of applying the composition on the substrate.

According to one aspect, the invention provides for non-therapeutic benefits.

Thus, according to yet another aspect of the invention there is provided use of a composition comprising 0.01 to 5% by weight thymol, 0.01 to 5% by weight terpineol, and a carrier for faster reduction in microbial count.

According to yet another aspect of the invention there is provided use of a composition comprising 0.01 to 5% by weight thymol, 0.01 to 5% by weight terpineol, and a carrier for improved hygiene of surfaces of human body. Human surfaces include skin, hands and oral cavity. A preferred aspect provides for use of a composition comprising 0.01 to 5% by weight thymol, 0.01 to 5% by weight terpineol, and a carrier for improved hand hygiene. Yet another preferred aspect provides for use of a composition comprising 0.01 to 5% by weight thymol, 0.01 to 5% by weight terpineol, and a carrier for improved oral hygiene.

The invention also provides for therapeutic benefits.

Thus, according to yet another aspect of the invention there is provided a composition comprising 0.01 to 5% by weight thymol, 0.01 to 5% by weight terpineol, and a carrier for faster reduction in microbial count.

According to yet another aspect of the invention there is provided use of a composition comprising 0.01 to 5% by weight thymol, 0.01 to 5% by weight terpineol, and a carrier for improved hygiene of surfaces of human body.

EXAMPLES

The invention will now be demonstrated with examples. The examples are for purpose of illustration only and do not limit the scope of claims in any manner.

Examples 1 to 3

Synergistic Interaction Between Thymol and Terpineol in Providing Bacterial Kill in Short Time Frames (15 Seconds)

Compositions comprising each individual active and a combination were prepared with water as a carrier (details given in Table 1 below). Terpineol and thymol were obtained from Nishant aromas, India.

About $10^7$ bacterial cells (*E. coli* ATCC 10536) were taken in a test tube and contacted with various compositions for a period of 15 seconds. Bacteria were taken out after 15 seconds of contact and presence of viable cells was determined by serial dilution and plating on agar plates. The data is presented in log (Viable *E. Coli*) which is the $\log_{10}$ of the number of viable *E. Coli* remaining after 15 seconds of contact. Thus if $10^4$ remained, log (Viable *E. Coli*) is 4.

TABLE 1

Antimicrobial efficacy of Thymol and Terpineol

| Ex No | Composition | Log (Viable *E. coli*) |
|---|---|---|
| 1 | Thymol (0.2%) | 3.1 |
| 2 | Terpineol (0.5%) | 6.3 |
| 3 | Thymol (0.2%) + Terpineol (0.5%) | No bacteria remaining |

The data in Table 1 indicates that there is a synergistic interaction between thymol and terpineol in providing antibacterial kill in very short time frames.

Examples 4 to 9

Effect of Other Antibacterial Combinations on Bacterial Kill in Short Time Frames (15 seconds)

Experiments similar to Examples 1 to 3 were carried out with various other antibacterial combinations as shown in Table 2. Eucalyptol and linalool were obtained from Fluka.

Menthol, citral, and geraniol were obtained from Som Santi Corporation, India. $10^8$ bacterial cells (*E. coli* ATCC 10536) were taken initially.

The data in log (Viable *E. Coli*) for the various combinations after 15 seconds of contact time is presented in Table 2.

TABLE 2

Antimicrobial efficacy

| Ex No | Composition | Log (Viable *E. coli*) |
|---|---|---|
| 4 | Thymol (0.2%) + Linalool (0.5%) | 3.4 |
| 5 | Thymol (0.2%) + Citral (0.5%) | 5.0 |
| 6 | Thymol (0.2%) + Geraniol (0.5%) | 4.1 |
| 7 | Menthol (0.2%) + Terpineol (0.5%) | 5.0 |
| 8 | Eucalyptol (0.2%) + Terpineol (0.5%) | 2.1 |
| 9 | Triclosan (0.2%) + Terpineol (0.5%) | 5.0 |

The data in Table 2 indicates that various other combinations of well known compounds of similar class as thymol and terpineol are not capable of providing the fast antibacterial action.

Example 10 to 13

Effect of Combination of Thymol and Terpineol in Inhibiting Growth of Various Other Bacteria in Comparison to TCC The combination of thymol (0.2%) and terpineol (0.5%) was tested for its efficacy in inhibiting growth of various other bacteria after they are contacted with this combination for about 15 seconds. Similar experiments were carried out with another well known antibacterial active TCC (trichloro carbanilide). The experiments were carried out similar to those of Examples 1 to 3 and the data on the viable bacteria remaining after contact with the actives for 15 seconds is summarized in Table 3

TABLE 3

Antimicrobial efficacy of actives with various bacteria

| Ex No | Organism | Culture added Log (CFU/ml) | 0.2% TCC Log (CFU/ml) | 0.2% Thymol + 0.5% Terpineol Log (CFU/ml) |
|---|---|---|---|---|
| 10 | *Klebsiella* | 7.35 | 7.28 | 3.4 |
| 11 | *Entereobacter* | 6.87 | 6.87 | 5.0 |
| 12 | *Salmonella* | 7.63 | 7.33 | 4.1 |
| 13 | *Vibrio cholerae* | 7.58 | 7.20 | 5.0 |

The data in Table 3 indicates that the composition of the invention is active against a large number of bacteria encountered when cleaning various substrates while a well known antibacterial (TCC) does not provide such efficacy.

Examples 14-17

Anti-Bacterial Efficacy of Soaps Containing Various Antibacterial Actives

Soap bars (containing 72 TFM soap) were prepared containing various antibacterial actives. These soap bars were tested in in-vitro assays as per the procedures used in Examples 1-3. The sample used in the assays was an 8% aqueous solution of the soap bars. The amount of *E-Coli* added initially was about $10^7$. The various soap bars prepared and the results of the antibacterial efficacy in terms of viable bacteria remaining after contact with the actives for 15 seconds is summarized in Table 4.

TABLE 4

| Ex. No | Composition | Log (CFU/ml) |
|---|---|---|
| 14 | Soap | 6.35 |
| 15 | Soap with 0.2 wt % carvacrol | 6.02 |
| 16 | Soap with 0.2% carvacrol + 0.5% Terpineol | 6.78 |
| 17 | Soap with 0.2% Thymol + 0.5% Terpineol | 5.21 |

Carvacrol is an isomeric form of thymol. The data in Table 4 indicates that a soap bar prepared with the composition of the invention (Example 17) is superior to soap bars prepared without any antibacterial active or with other antibacterial actives, some of the actives therein having a structure similar to thymol.

Examples 18 to 21

Antibacterial Activity of Soap Compositions in Washing Hands Artificially Contaminated with Bacteria The following protocol was used to test the antibacterial efficacy of various compositions in its ability to remove bacteria which is added to the human hands.

Both hands of volunteers were first disinfected to remove the normal flora of the hands. 100 microlitres of *E. coli* suspension (corresponding to about $10^7$ CFU/ml) was applied to both the volunteer's hands. One hand was washed with a soap solution containing 8% soap but with no antibacterial active present in the soap solution. The other hand was washed with soap containing one or more antibacterial active. The hands were washed for 15 seconds by the investigator.

Thereafter, for recovery of bacteria remaining on the volunteer's hands the following treatment was carried out. The hand was placed in a sterile polyethylene bag containing 75 ml of collection fluid (Butterfield phosphate buffer with neutralizers) and secured above the wrists with rubber bands. Recovery of bacteria was carried out using a hand washing machine where the polyethylene bag was scrubbed on the outside with mechanized brushes for predetermined period of time during which most of the bacteria were scrubbed off the hands and dispersed in the collection fluid. The samples were immediately diluted and plated onto CY agar. The antibacterial efficacy in terms of viable bacteria remaining on the hand after washing it with the soap composition for 15 seconds is summarized in Table 5.

TABLE 5

| Example | Composition | Log (Viable *E. coli* remaining) |
|---|---|---|
| 18 | Soap | 4.00 |
| 18A | Soap with 0.2% thymol | 3.51 |
| 19 | Soap | 4.06 |
| 19A | Soap with 0.5% terpineol | 4.10 |
| 20 | Soap | 3.30 |
| 20A | Soap with 0.2% carvacrol and 0.5% terpineol | 3.43 |
| 21 | Soap | 5.23 |
| 21A | Soap with 0.2% thymol and 0.5% terpineol | 4.32 |

The data in Table 5 indicates that a soap composition of the invention (Example 21A) provides vastly superior antibacterial efficacy in comparison to a soap composition not having either thymol or terpineol (Example 21). In comparison no such superior benefits are seen in anti bacterial containing soap as compared to the respective controls (Examples 18A, 19A and 20 A in comparison to Examples 18, 19, and 20).

Examples 22 and 23

Continued Protection

The ability of the composition of the invention to provide continued protection on hands washed with the composition of the invention was investigated. The protocol was as given below.

One hand of a volunteer was washed with a 8% solution of a 72 TFM soap (containing no antibacterial active). The other hand was washed with a similar soap but additionally containing 0.5% terpineol and 0.2% thymol for 15 seconds by the investigator. The hands were allowed to air dry.

Three areas each of ~2.8 cm$^2$ were marked on both the palms. At times of 0 minutes, 30 minutes and 60 minutes, 25 microliters corresponding to about 10$^6$ E. coli cells were applied on each area. After 5 mins the bacteria were recovered using a Teflon cup and rod and the bacteria were enumerated using CY agar. The antibacterial efficacy in terms of viable bacteria remaining on the hand after the above procedure is summarized in Table 6.

TABLE 6

| Example | Composition | Log (Viable E. coli remaining) | | |
|---|---|---|---|---|
| | | 0 minutes | 30 minutes | 60 minutes |
| 22 | Soap | 5.70 | 5.67 | 5.25 |
| 23 | Soap with 0.2% thymol and 0.5% terpineol | 1.48 | 1.96 | 1.69 |

The data in Table 6 indicates that a soap composition as per the invention (Example 23) provides for continued protection on hand as compared to a soap composition outside the invention.

Examples 24-29

Antibacterial Activity of the Composition of the Invention Against Oral Bacteria The anti-bacterial activity of the composition of the invention against a commonly found Gram positive oral bacteria viz. *Streptococcus mutans* ATCC 25175 and a Gram negative oral bacteria *Neisseria subflava* ATCC 19243) was determined. This was investigated using Oxoplates. Oxoplates monitor oxygen depletion within the reaction system (containing bacteria, broth and actives).

Bacteria

A Gram positive (*Streptococcus mutans* ATCC 25175) and a Gram negative (*Neisseria subflava* ATCC 19243) bacterium were selected for testing the active solutions. Both bacteria were grown on BHIS agar plates for 24 hours at 37° C./15% $CO_2$, they were then suspended in PBS to a McFarland standard of 2 (~6×10$^8$ cells).

Solutions

Each active was dissolved in 50% ethanol solutions for testing. All solutions were made at 10 times concentrated to allow for dilution in the plate. Reduced concentrations were used for *N. subflava* due to the greater sensitivity of this organism to biocides, Oxoplate Method The following components were placed into the wells of the Oxoplates,
170 □l BHI broth
20 □l test solution
10□l bacteria The broth was placed into the Oxoplate first, followed by the test solution, and then the bacterium. Water or 50% ethanol controls were also used in each plate. All solutions were tested in replicates of four. The plates were placed into the fluorescent plate reader, incubated at 37° C. and measured every 15 minutes for 18 hours. The sensors on the bottom of the wells were measured at 2 wavelengths,
Indicator (650/540 nM)
Reference (590/540 nm).

The oxygen concentration was calculated using these values and a calibration performed for maximum and minimum oxygen concentration. A graph was then plotted of the oxygen depletion curves over the 18 hour period, which was used to determine the level at which the bacteria start to deplete the oxygen. The following Table 7 shows the concentration of the active at which no oxygen depletion was observed indicating no growth of the bacteria.

TABLE 7

| Example No | Bacteria | Concentration of active (wt %) at no growth |
|---|---|---|
| 24 | Streptococcus mutans | Terpineol (0.4%) |
| 25 | Streptococcus mutans | Thymol (0.08%) |
| 26 | Streptococcus mutans | Terpineol (0.1%) + Thymol (0.04%) |
| 27 | Neisseria subflava | Terpineol (0.08%) |
| 28 | Neisseria subflava | Thymol (0.02%) |
| 29 | Neisseria subflava | Terpineol (0.03%) + Thymol (0.012%) |

The data in Table 7 indicates that there is synergistic interaction between thymol and terpineol in inhibiting growth of bacteria found in the oral cavity.

The minimum concentration for inhibiting growth of *Streptococcus mutans* in the above examples was 0.1% terpineol in combination with 0.04% thymol, and the concentration for inhibiting growth of *Neisseria subflava* was 0.03% terpineol (0.03%) in combination with 0.012% thymol. However, it is preferred that the concentration for inhibiting growth of oral microbes in faster time is in the range of 0.05 to 5 wt % thymol in combination with 0.05 to 5 wt % terpineol.

Examples 30-33

Soap Compositions Prepared with Varying Amounts of Thymol and Terpineol

Various soap bars (of 72 TFM) were prepared with the antibacterial actives as shown in Table 8. The bars were assessed for acceptability of odour impact by a trained perfumery expert. The ratings are given in Table 8.

TABLE 8

| Example No | Composition | Perfumery assessment |
|---|---|---|
| 30 | Soap with 0.2% thymol and 0.5% terpineol | Highly acceptable |

TABLE 8-continued

| Example No | Composition | Perfumery assessment |
|---|---|---|
| 31 | Soap with 0.4% thymol and 1.0% terpineol | Acceptable but less preferred |
| 32 | Soap with 0.8% thymol and 2% terpineol | Acceptable but less preferred |
| 33 | Soap with 8% thymol and 8% terpineol | Unacceptable |

From the results of all of the above examples, it is clear that specific mixture of terpineol with thymol of the present invention provides fast antimicrobial action with relatively high anti microbial efficacy as compared to prior art compositions. The results further demonstrate that the mixture of terpineol with thymol provides synergistically fast antimicrobial action with relatively high anti microbial efficacy as compared to terpineol alone or thymol alone.

The invention claimed is:

1. A method of disinfecting a surface of the human body comprising the steps of:
   (i) applying a composition comprising:
      a. 0.1 to less than 0.3% by weight thymol;
      b. 0.1 to less than 1% by weight terpineol, and
      c. a carrier onto the surface of the human body; and
   (ii) rinsing the surface with a suitable solvent or wiping the surface with a suitable wipe,
   wherein said step of rinsing or wiping the surface is carried out less than a minute after the step of applying the composition.

2. The method as claimed in claim 1 wherein the composition further comprises from 1 to 80% by weight surfactant.

3. The method as claimed in claim 1 wherein the composition is applied to the hands in an aqueous base for skin cleansing.

4. The method as claimed in claim 1 wherein the composition is applied to the oral cavity for improved oral hygiene.

5. The method as claimed in claim 1 wherein the step of rinsing or wiping the surface is carried out not more than 15 seconds after the step of applying the composition.

* * * * *